(12) United States Patent
Chen et al.

(10) Patent No.: US 8,004,668 B2
(45) Date of Patent: Aug. 23, 2011

(54) FLUORESCENT COLOR CALIBRATOR FOR CALIBRATING RGB PIXEL VALUES

(76) Inventors: Jiuan-Jiuan Chen, Arlington, MA (US); Paul Messier, Brighton, MA (US)

( * ) Notice: Subject to any disclaimer, the term of this patent is extended or adjusted under 35 U.S.C. 154(b) by 123 days.

(21) Appl. No.: 12/488,565

(22) Filed: Jun. 21, 2009

(65) Prior Publication Data

US 2010/0321681 A1    Dec. 23, 2010

(51) Int. Cl.
*G01J 1/10* (2006.01)
(52) U.S. Cl. .................. 356/243.1; 356/243.5; 356/300; 356/406; 356/419
(58) Field of Classification Search .................. 356/325, 356/320, 300, 402, 326, 243.1, 419; 382/128
See application file for complete search history.

(56) References Cited

U.S. PATENT DOCUMENTS

| | | | | |
|---|---|---|---|---|
| 3,832,070 | A * | 8/1974 | Cox | 356/445 |
| 6,008,907 | A * | 12/1999 | Vigneau et al. | 358/1.9 |
| 6,348,965 | B1 * | 2/2002 | Palladino et al. | 356/243.1 |
| 7,072,036 | B2 * | 7/2006 | Jones et al. | 356/246 |
| 7,180,524 | B1 * | 2/2007 | Axelrod | 345/593 |
| 7,416,701 | B2 * | 8/2008 | Tokhtuev et al. | 422/82.08 |
| 7,480,042 | B1 * | 1/2009 | Phillips et al. | 356/243.1 |

* cited by examiner

*Primary Examiner* — Tarifur R. Chowdhury
*Assistant Examiner* — Isiaka O Akanbi

(57) ABSTRACT

A fluorescent color calibrator for calibrating RGB pixel values is provided. The fluorescent color calibrator includes a plurality of fluorogenic compounds adapted to fluoresce in a visible color spectrum; and a second plurality of fluorogenic compounds adapted to fluoresce in multiple visible gray spectrums. Also provided is a method for using the fluorescent color calibrator to standardize fluorescent colors when viewing with an RGB monitor.

18 Claims, 4 Drawing Sheets

| LOW INTENSITY FLOURESCENT COLOR SPACE (RGB) BEFORE VALUES | RED | GREEN | BLUE |
|---|---|---|---|
| R | 65 | 15 | 4 |
| O-R | 175 | 49 | 10 |
| Y-O | 125 | 160 | 14 |
| Y-G | 75 | 67 | 12 |
| G | 89 | 71 | 15 |
| B | 9 | 22 | 45 |
| DG | 134 | 161 | 175 |
| LG | 156 | 175 | 166 |

FIG. 6A

| LOW INTENSITY FLOURESCENT COLOR SPACE (RGB) TARGET VALUES | RED | GREEN | BLUE |
|---|---|---|---|
| R | 73 | 12 | 8 |
| O-R | 192 | 44 | 2 |
| Y-O | 150 | 142 | 0 |
| Y-G | 51 | 86 | 10 |
| G | 47 | 85 | 9 |
| B | 0 | 38 | 29 |
| DG | 169 | 162 | 163 |
| LG | 198 | 186 | 189 |

FIG. 6B

FLUORESCENT COLOR CALIBRATOR FOR CALIBRATING RGB PIXEL VALUES

BACKGROUND

1. Field of Use

These teachings relate generally to a fluorescent color calibration apparatus and more particularly to providing a fluorescent color standard or reference within photographic or imaged areas for calibrating RGB values.

2. Description of Prior Art (Background)

The photographic documentation of fluorescence in various fields, including art conservation, forensics, gemology and medicine, lacks a standard for calibrating fluorescent color balance. As a result, the interpretation of fluorescent colors is highly subjective and, therefore, the potential evidentiary value of photographic documentation of fluorescence is limited. Numerous variables such as the intensity of the UV radiation, the distance between the UV radiation source and the fluorescing materials, wavelength variations in UV radiation sources and camera specific variables (such as white balance), make the meaningful comparison between one set of UV photographic documentation and another set of UV photographic documentation nearly impossible. In addition, all light sources currently used in fluorescent photography lack stability over long periods. This lack of stability causes the output of a xenon lamp, for example, to fluctuate as a function of time, which affects fluorescence intensity of a given photograph, all other conditions being equal. To perform accurate and comparable photographic fluorescent color analyses, these light source fluctuations must be taken into account. In general, the intensity from a UV lamp is quite consistent. Unlike a tungsten bulb which can be dimmed to lower the intensity, a UV lamp has the same UV output. However, intensity can be adjusted intentionally, or unintentionally, in two ways: one is to move the lamp away or closer to the object; the other is use a higher or lower wattage UV bulb.

There is no prior product available on the market though there is some haphazard use of various florescent materials the might be familiar to the end user. A ruler is available through the Lighting Powder Company LLC which is advertised for forensic documentation. The ruler's orange ink exhibits sections of different fluorescent intensity when exposed to UV sources. While somewhat useful for recording the intensity of florescence, use of the ruler for color corrections is not possible. In addition, the high fluorescence end of the ruler actually produces an orange light that can skew the color balance; especially of images made to record low/moderate fluorescence. Likewise, there are fluorescent rulers primarily used for forensic investigation. These rulers will fluoresce (typically an orange color) under long wave ultraviolet radiation. The ruler also contains different sections to indicate the intensity of the fluorescence and can be used to indicate whether short wave ultraviolet was used as the excitation source. Such devices are limited in that the fluorescence is not consistent and can not be correlated to a range of measured or standard values. Therefore these devices are ineffective for color correcting recorded fluorescence.

Past practice also relied on a few known fluorescent colors, such as shellac, rose madder, or zinc white which are used as reference colors. These fluorescent colors are not consistent due to natural variability and manufacturing methods. Also the range of color offered by these materials covers only off-white, pink, and orange.

Other approaches rely on including various fluorescence materials into a photographic image documenting fluorescence. Materials like zinc white, rose madder, or shellac have characteristic fluorescence behaviors that those skilled in the field will visually recognize. However, the fluorescent properties of these materials vary greatly from one source to another and thus cannot be used for accurate calibration. Fluorescent "rulers" can provide a qualitative sense of the intensity of the fluorescence but not color information. Typically, the color and intensity of UV fluorescence is corrected, if at all, "by eye", thus undermining the evidentiary value of such documents.

Also, the intensity of fluorescence also varies greatly from one material to another. Most naturally occurring organic materials have some fluorescence, though this fluorescence can be very low. On the other hand, many synthetic materials have extremely high levels of fluorescence. Use of a single standard for both very bright fluorescence and dim fluorescence is unacceptable due to the sensitivity range of both the traditional silver halide emulsions (analog photographic) and/or digital cameras. If one uses only one reference card (with a fixed brightness) then it might not be possible to record fluorescent colors (both from the object and reference card) with correct color saturation if the object and the reference card have significantly different brightness. If the object has strong fluorescence, like a painting painted with day-glow pigments, the correct exposure time for the camera needs to be short. In this case a reference card might appear too dark due to underexposure. If the reference card is too dark (or too light) then the measured fluorescent values are not applicable and the image cannot be color corrected. Therefore, to compensate for fluorescent intensity differences, two or more fluorescent color standards are needed to more precisely capture the fluorescence behavior of materials with high and low fluorescent intensity.

It will be appreciated that there is no known existing standard for calibrating or adjusting a photographic record of visible fluorescence colors. In addition, single standards, such as white standards (made of barium sulfate) used to calibrate UV spectrophotometers are expensive as well as hazardous.

BRIEF SUMMARY

The foregoing and other problems are overcome, and other advantages are realized, in accordance with the presently preferred embodiments of these teachings.

As will be described below, important aspects of the invention reside in the invention for providing at least one fluorescent color range standard or reference within photographs made using long (UV A) and short wave (UV C) ultraviolet radiation. Use of the standards will enable users to color correct photographic documentation of florescence and allow the objective comparison of fluorescence captured under various conditions by various photographers. The fluorescent color standard is subsequently usable in the calibration of computer monitors or screen RGB color values used to portray the photographic or imaged areas. The fluorescent color standard is exposed under known, or unknown, ultraviolet (UV) light exposure conditions simultaneously with the UV light exposure of the corresponding photographic or imaged areas. In addition to handling and development procedures, the paired fluorescent color standard and photographs, or images, exposed to the same ultraviolet light are also subjected to the same environmental conditions, e.g., UV lamp types, photography equipment, cameras, filters and other variables used to create the photograph or image. Consequently, RGB deviations from the fluorescent color standard values are measurable to provide an absolute reference which the corresponding RGB values in the photographic or imaged areas can be compared and adjusted.

In accordance with one embodiment of the invention a fluorescent color calibrator for calibrating RGB pixel values is provided. The fluorescent color calibrator includes a fluorogenic compound adapted to fluoresce in a visible color spectrum and a second fluorogenic compound co-located with the first fluorogenic compound and is adapted to fluoresce in a visible gray spectrum.

In accordance with another embodiment the invention includes a program storage device for containing a method for calibrating RGB pixel values of a target object imaged with UV light sources and displayed by a computer program. The method determines a standard RGB fluorescence value by selecting and illuminating a fluorogenic compound with a known UV source. The method also includes measuring the visible emission spectra of the florescent spectra of the fluorogenic compound and determining the RGB values of the measured emission spectra produces standard RGB values. The method also includes co-locating and illuminating a target object and the fluorogenic compound with a second UV source. A target object may be a painting, photograph, gem stone, or any object or material that may exhibit fluorescence when illuminated by a UV source. The method images (e.g. photographs) the co-located target object and the fluorogenic compound illuminated with the second UV source. Next, with a computer program (e.g., Adobe Photoshop) the method displays the imaged co-located target object and the fluorogenic compound and adjusts the computer program to display the standard RGB values.

The invention is also directed towards a fluorescent color calibrator for calibrating RGB pixel values. The fluorescent color calibrator includes a substrate and a plurality of fluorogenic compounds attached to the substrate and adapted to fluoresce in a visible color spectrum include: a substantially magenta fluorogenic compound; a substantially orange-red fluorogenic compound; a substantially yellow-orange fluorogenic compound; a substantially yellow-green fluorogenic compound; a substantially green fluorogenic compound; and a substantially blue fluorogenic compound. The invention also includes a plurality of second fluorogenic compounds attached to the substrate and adapted to fluoresce in a visible gray spectrum. The plurality of second fluorogenic compounds includes; a substantially gray fluorogenic compound; and a second substantially gray fluorogenic compound exhibiting a darker gray fluorescence relative to the first substantially gray fluorogenic compound. Included with the invention is an overlay cutout affixed to the substrate and adapted to allowing imaging of the plurality of first fluorogenic compounds and the plurality of second fluorogenic compounds.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIG. 6A is a representative table of RGB values associated with the photographic image shown in FIG. 5 before the RGB values are adjusted to the target RGB values.

FIG. 6B is a representative table of standard RGB values associated with the fluorescent color calibrator standard shown in FIG. 1 and FIG. 5.

DETAILED DESCRIPTION

Figure 1:
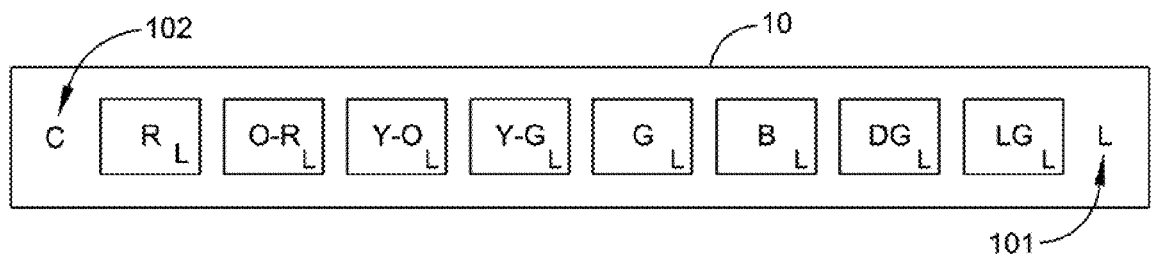
FIG. 1 is a top-down pictorial illustration of one embodiment of the present fluorescent color calibrator standard in accordance with an embodiment of the present invention.

As is well known in the art, fluorescence occurs when a molecule absorbs light photons from a UV-visible light spectrum, known as excitation, and then rapidly emits light photons as it returns to its ground state. Fluorimetry characterizes the relationship between absorbed and emitted photons at specified wavelengths. It is a precise quantitative analytical technique that is inexpensive and easily mastered.

All chemical compounds absorb energy which causes excitation of electrons bound in the molecule, such as increased vibrational energy or, under appropriate conditions, transitions between discrete electronic energy states. For a transition to occur, the absorbed energy must be equivalent to the difference between the initial electronic state and a high-energy state. This value is constant and characteristic of the molecular structure. This is termed the excitation wavelength.

If conditions permit, an excited molecule will return to ground state by emission of energy through heat and/or emission of energy quanta such as photons. The emission energy or wavelength of these quanta are also equivalent to the difference between two discrete energy states and are also characteristic of the molecular structure.

Fluorescence occurs when a molecule absorbs photons from the UV-visible light spectrum (200-900 nm), causing transition to a high-energy electronic state and then emits photons as it returns to its initial state, on the order of less than $10^{-9}$ sec. Some energy, within the molecule, is lost through heat or vibration so that emitted energy is less than the exciting energy; i.e., the emission wavelength is always longer than the excitation wavelength. The difference between the excitation and emission wavelengths is called the Stokes shift.

Fluorescent compounds or fluorophors can be identified and quantified on the basis of their excitation and emission properties. The excitation and emission properties of a compound are fixed, for a given instrument and environmental condition, and can be used for identification and quantification.

Although, maximum emission occurs only for specific excitation and emission wavelength pairs, the magnitude of fluorescent intensity is dependent on both intrinsic properties of the compound and on readily controlled experimental parameters, including intensity of the absorbed light and concentration of the fluorophor in solution. The intensity of the excitation light, which impinges on the sample, depends of the source type, wavelength and other instrument factors. The light source, usually mercury or xenon, has a characteristic spectrum for emission intensity relative to wavelength. At high dye concentrations or short path lengths, fluorescence intensity relative to dye concentration decreases as a result of "quenching". As the concentration of molecules in a solution increases, probability increases that excited molecules will interact with each other and lose energy through processes other than fluorescent emission. By using two standards, materials of high and low intensity fluorescence can be color corrected and objectively compared. By incorporating materials that fluorescence only under long wave ultraviolet, the reference cards can indicate which of the commonly used wavelengths (long or short wave ultraviolet) was used to induce the recorded fluorescence.

Referring now to FIG. 1 there is shown a top-down pictorial illustration of one embodiment of the present fluorescent color calibrator standard 10. It will be appreciated that although the present invention will be described with reference to the embodiments shown in the drawings, it should be understood that the present invention can be embodied in many alternate forms of embodiments. In addition, any suitable size, shape or type of elements or materials could be used.

Still referring to FIG. 1, the fluorescent color calibrator standard 10 includes an indicator 102 for indicating that the standard is, or has been, illuminated with an ultra violet light (UV) source. The standard 10 also includes another indicator 101 for indicating that the UV source is, or was, a low intensity UV source. Each of the fluorescent color patches or chips, corresponds to the fluorescent colors red, orange-red, yellow-orange, yellow-green, green, blue, darker-gray, lighter-gray, respectively. It will be appreciated that each of the fluorescent colors may be comprised of any suitable organic and/or inorganic fluorogenic material. As will be discussed herein each of the fluorescent colors is mapped to a standard Red-Green-Blue (RGB) value set using a spectrometer. The fluorescent paint chips are illuminated with appropriate UV lamps, such as, for example, a high-mercury pressure UV lamp for UVA. The spectrometer software may be adjusted to "colorimeter mode," to record the emission of the visible fluorescence from the paint chips. The colorimeter mode provides readings in any number of color spaces, such as Munsell, or CIE L*a*b* values, which are then translated into the standard low-fluorescent intensity RGB values described herein and shown in FIG. 6. It should be understood that the RGB values shown in FIG. 6 are for exemplary purposes only.

Figure 2:
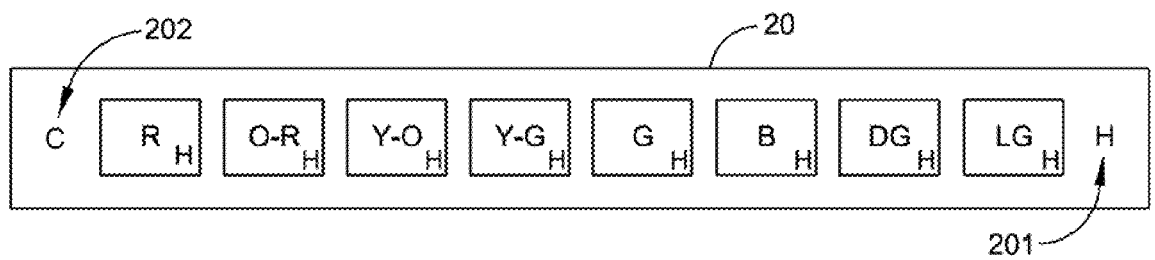
FIG. 2 is a top-down pictorial illustration of another embodiment of the present fluorescent color calibrator standard invention shown in FIG. 1.

Referring also to FIG. 2 there is shown a top-down pictorial illustration of another embodiment of the present fluorescent color calibrator standard 20. The fluorescent color calibrator standard 20 includes an indicator 202 for indicating that the standard is, or has been, illuminated with an ultra violet light (UV) source. The standard 20 also includes another indicator 201 for indicating that the UV source is, or was, a high intensity UV source. Each of the fluorescent color patches or chips are comprised of fluorogenic compounds such as available from Golden Artist Colors Inc., and correspond to the fluorescent colors red (or magenta), orange-red, yellow-orange, yellow-green, green, blue, darker-gray, lighter-gray, respectively. It will be understood that reference to a colored fluorescent compound means that the compound fluoresces in that color. It will again be appreciated that each of the fluorescent colors may be comprised of any suitable organic and/or inorganic fluorogenic material. Similar to the earlier discussion each of the fluorescent colors is mapped to a high-fluorescent intensity standard Red-Green-Blue (RGB) value set using a spectrometer. The fluorescent paint chips are illuminated with appropriate UV lamps, such as, for example, UVC lamp for high intensity fluorescent emissions. Likewise, the spectrometer software may be adjusted to "colorimeter mode," to record the emission of the visible fluorescence from the paint chips. The colorimeter mode provides readings in any number of color spaces, such as Munsell, or CIE L*a*b* values, which are then translated into the standard high-fluorescent intensity RGB values described herein.

Figure 3:
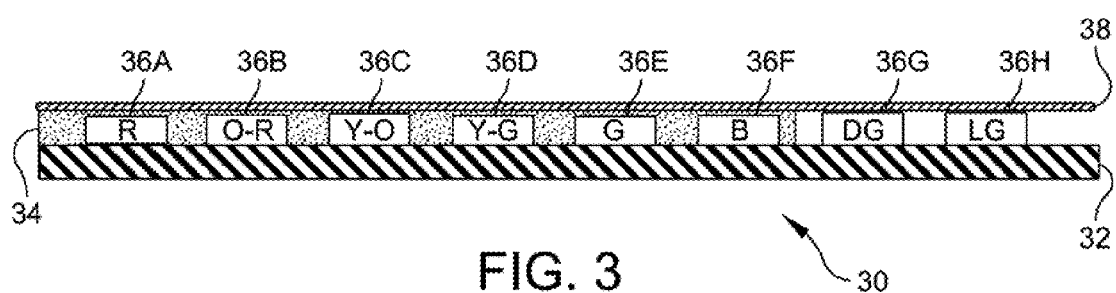
FIG. 3 is a side-view pictorial illustration of either the low intensity embodiment or the high intensity embodiment of the present fluorescent color calibrator standard shown in FIG. 1 and FIG. 2, respectively.

Referring also to FIG. 3 there is shown a side-view pictorial illustration of either the low intensity embodiment or the high intensity embodiment of the present fluorescent color calibrator standard 30. As will be discussed herein the low or high intensity determinants are the selection and formulation of the UV inhibiting coating 34 and the spectrometer illumination. It will be appreciated that this approach advantageously overcomes the prior art approach to reduce the intensity of fluorescence by adding material that does not fluoresce such as a carbon black pigment. It is also understood that the prior art approach alters both the intensity of the fluorescence and the color. Such color changes are unacceptable for standardization.

Still referring to FIG. 3 there is shown fluorescent paint chips 36A-36H. Fluorescent paint chips 36A-36H are waterborne acrylic paints produced from polymer coated dyes derived from suitable florescent pigments and dyes, and are coated or suitably attached onto the paperboard support 32. The paperboard support 32 which may be any suitable support such as resin coated paper.

Still referring to FIG. 3, the UV blocking coating 34 is then applied over the Fluorescent color paint chips 36A-36F. The predetermined UV blocking coating 34 may be any suitable blocking coating and layer thickness chosen for either low-intensity fluorescence or high-intensity fluorescence. For example, a foil strength UV blocking coating or low strength (1/20) blocking coating or layer may be used for low-intensity fluorescence or high-intensity fluorescence, respectfully.

It will be understood and appreciated that the light gray and dark gray paint chips are not UV blocked with UV blocking coating 34. It will be understood the gray chips advantageously provide visual information about the duration of exposure—brighter grays recorded longer exposure; darker, shorter exposure. In an indirect way, one can get a sense from the brightness of the grays how strong the object fluoresces—brighter grays, weak object fluorescence; darker grays, bright object fluorescence.

Also shown in FIG. 3 is overlay 38 which has suitable openings to expose all the fluorescent colors. Overlay 38 is also suitably marked with "H uv/vis" or "L uv/vis" with fluorophores sensitive to UVA and UVC, respectively, i.e., fluoresces when exposed to a high intensity or low intensity UV source, respectively. Overlay 38 is also marked "C" with fluorophores sensitive only to UVC.

Figure 4:
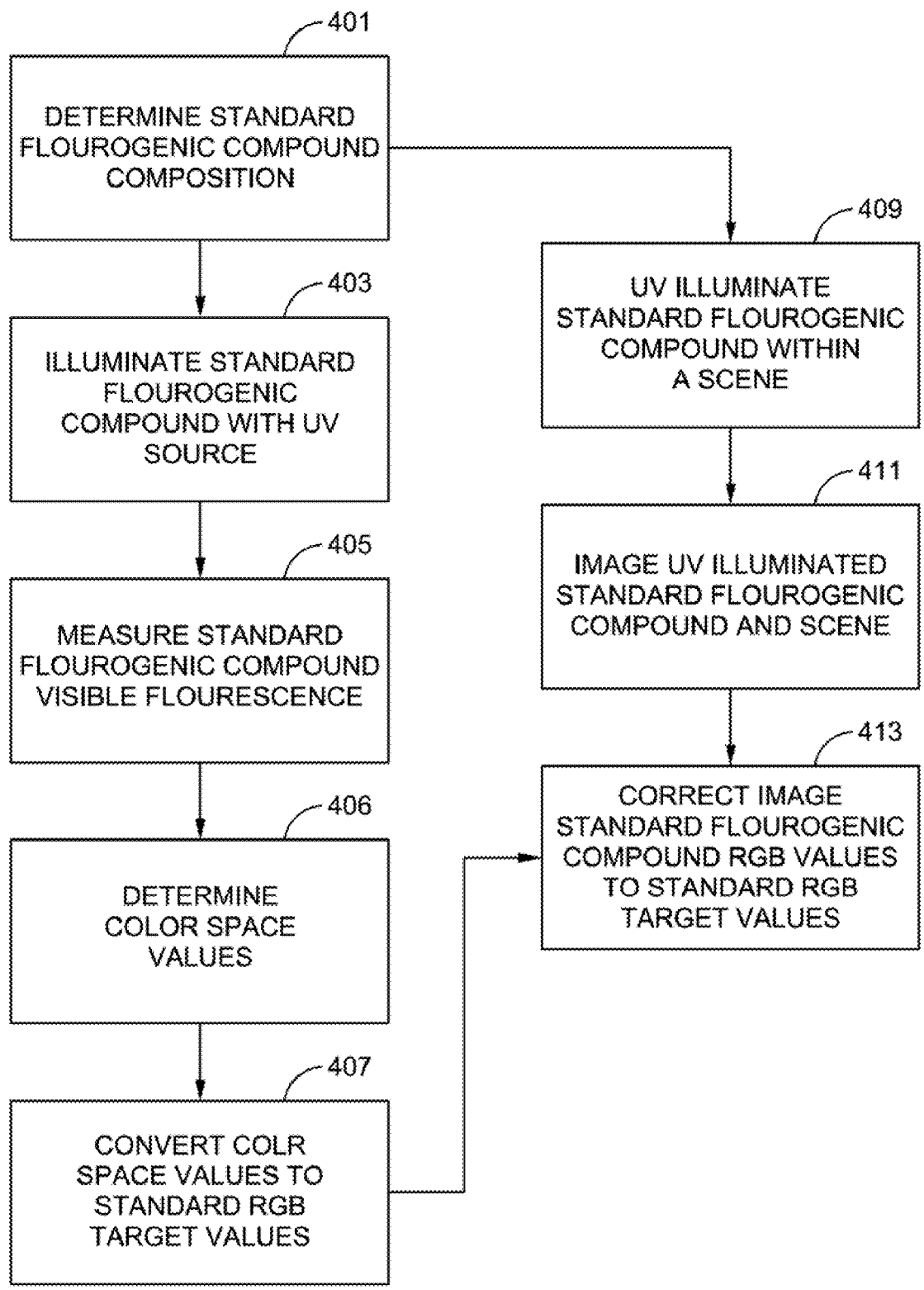
FIG. 4 is flowchart illustrating one method for determining and using the fluorescent standards shown in FIG. 1 and FIG. 2.

Turning now to FIG. 4 there is shown one method for determining and using the fluorescent standards described herein. Step 401 determines the standard fluorogenic compound (SFC) to use for a desired fluorescent color. After coating the SFC with the desired UV inhibitor agent or blocker. Step 403 illuminates the SFC with a suitable UV light source. Step 405 measures the SFC fluorescence using a suitable spectrometer to record the emission of the visible fluorescence from the SFC. The spectrometer readings may be in any suitable color space value 406, such as Munsell, or CIE L*a*b* values, which are then translated 407 to the desired standard high or low fluorescent intensity RGB values.

Figure 5:
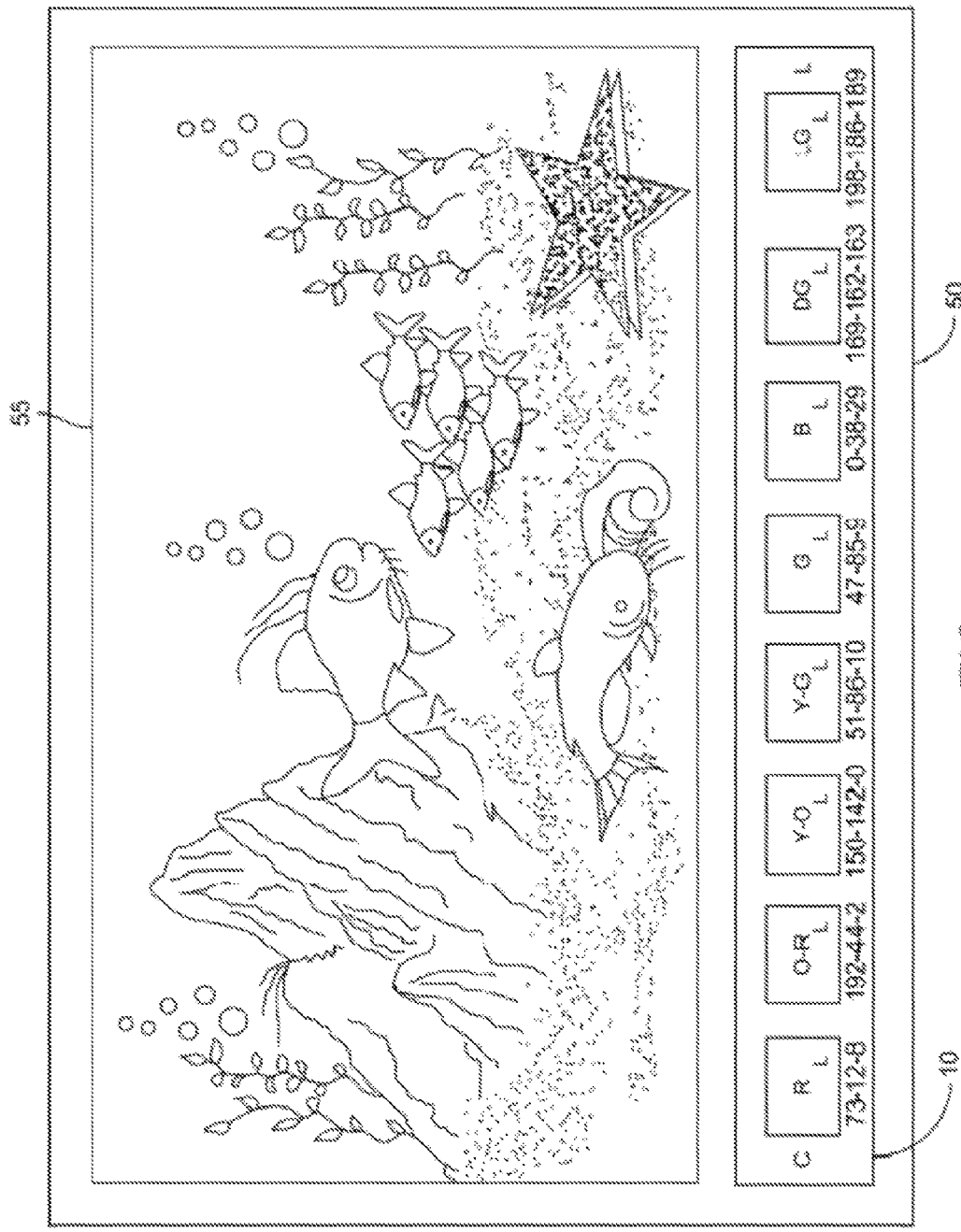
FIG. 5 is a pictorial representation of a photographic image of a scene exhibiting fluorescence and the fluorescent color calibrator standard shown in FIG. 1.

Referring also to FIG. 5 and again to FIG. 1, there is shown a pictorial representation of a photographic image 50 of a scene 55 exhibiting fluorescence and the fluorescent color calibrator standard 10 shown in FIG. 1. It will be understood that the scene 55 could be any suitable scene such as another photograph, image, or painting. It will also be understood that scene 55 could also be inorganic material such as a gem stone; or, organic material such as blood samples.

Step 409 UV illuminates the scene 55 and the fluorescent color calibrator standard 10. Step 411 images the illuminated scene 55 and the fluorescent color calibrator standard 10, for example, step 411 photographs the illuminated scene 55 and the fluorescent color calibrator standard 10 to produce FIG. 5: the pictorial representation 50 of the photographic of a scene 55 and the fluorescent color calibrator standard 10 shown in FIG. 1. It will be appreciated that the target RGB values may be printed on the calibrator standard 10 or otherwise provided as shown in FIG. 6B While viewing the pictorial representation 50 with any suitable software program, such as Adobe's Photoshop, on any suitable monitor, the RGB value of each fluorescent color chip or patch of the imaged standard is set to the predetermined high or low fluorescent intensity RGB standard for that particular color, step 413, as shown in FIG. 6B. It will be understood that the values shown in FIG. 6B are for illustration purposes only.

It will be appreciated that the present invention overcomes prior art problems associated with ultraviolet induced visible fluorescence photography where the present invention provides a fluorescence color range standard within photographs made using long (UV A) and short wave (UV C) ultraviolet radiation; the standard recorded in conjunction with the target object, e.g., a photograph, enables fluorescence phenomenon to be objectively corrected and compared. It is understood that the fluorescent standard recorded, or imaged, with the target object comprises consistent, predetermined values. Using these known values, false/erroneous color balance caused by human/instrumental error and numerous other variables e.g., type of UV lamps, photography equipment, cameras, filters and other variables used to create the photograph can be corrected. The present invention's relatively inexpensive dyes and coating materials also overcomes the problem of using expensive prior art white standards.

It should be understood that the foregoing description is only illustrative of the invention. Thus, various alternatives and modifications can be devised by those skilled in the art without departing from the invention. Accordingly, the present invention is intended to embrace all such alternatives, modifications and variances that fall within the scope of the appended claims.

What is claimed is:

1. A fluorescent color calibrator for calibrating RGB pixel values, the fluorescent color calibrator comprising:
    at least one first fluorogenic compound adapted to fluoresce in a visible color spectrum;
    a UV blocking agent coating affixed to the at least one first fluorogenic compound, wherein the UV blocking agent coating is a predetermined thickness; and
    at least one second fluorogenic compound co-located with the at least one first fluorogenic compound and adapted to fluoresce in a visible gray spectrum.

2. The fluorescent color calibrator as in claim 1 further comprising a substrate far affixing the at least one first fluorogenic compound and the at least, second fluorogenic compound.

3. The fluorescent color calibrator as in claim 2 wherein the substrate comprises resin coated paper.

4. The fluorescent color calibrator as in claim 1 further comprises an overlay cut-out for exposing the at least one first fluorogenic compound and the at least one second fluorogenic compound.

5. The fluorescent color calibrator as in claim 4 wherein the overlay cut-out further comprises a first fluorophor sensitive to UVA light sources.

6. The fluorescent color calibrator as in claim 4 wherein the overlay cut-out further comprises a second fluorophor sensitive to UVC light sources.

7. The fluorescent color calibrator as in claim 1, wherein the at least one first fluorogenic compound further comprises a plurality of first fluorogenic compounds, wherein the plurality of first fluorogenic compounds comprises:
    at least one magenta fluorogenic compound;
    at least one orange-red fluorogenic compound;
    at least one yellow-orange fluorogenic compound;
    at least one yellow-green fluorogenic compound;
    at least one green fluorogenic compound; and
    at least one blue fluorogenic compound.

8. The fluorescent color calibrator as in claim 1, wherein the at least one second fluorogenic compound further comprises a plurality of second fluorogenic compounds, wherein the plurality of second fluorogenic compounds comprises:
    a first gray fluorogenic compound; and
    a second gray fluorogenic compound exhibiting a darker gray fluorescence relative, to the first gray fluorogenic compound.

9. A program storage device readable by a machine, tangibly embodying a program of instructions executable by the machine to perform method steps for calibrating RGB pixel values of a target object imaged with UV light sources and displayed by a computer program, the method comprising:
    determining a first standard RGB fluorescence value, wherein determining the first standard RGB fluorescence value comprises:
        selecting a first fluorogenic compound illuminating, the first fluorogenic compound with a known UV source;
        measuring the visible emission spectra of florescent spectra of the first fluorogenic compound;
        determining the RGB values of the measured emission spectra;
    co-locating and illuminating the target object and the first fluorogenic compound with a second UV source;
    imaging the co-located target object and the first fluorogenic compound illuminated with the second UV source;
    displaying the imaged co-located target object and the first fluorogenic compound illuminated with the second UV source with the computer program; and
    adjusting the computer program to display the determined RGB values.

10. The method as in claim 9 wherein selecting the first fluorogenic compound further comprises;
    determining a first plurality of fluorogenic compounds;
    coating the first plurality of fluorogenic compounds with a UV blocking agent;
    determining a second plurality of fluorogenic compounds; and
    affixing the first plurality of fluorogenic compounds and the second plurality of fluorogenic compounds to a common substrate.

11. The method as in claim 10 wherein determining the first plurality of fluorogenic compounds further comprises:
    determining at least one magenta fluorogenic compound;
    determining at least one orange-red fluorogenic compound;
    determining at least one yellow-orange fluorogenic compound;
    determining least one yellow-green fluorogenic compound;

determining at least one green fluorogenic compound; and
determining at least one blue fluorogenic compound.

12. The method as in claim 10 wherein determining the second plurality of fluorogenic compounds further comprises:
determining a first gray fluorogenic compound; and
determining a second gray fluorogenic compound exhibiting a darker gray fluorescence relative to the first gray fluorogenic compound.

13. The method as in claim 12 wherein determining the first plurality and the second plurality of fluorogenic compounds further comprises determining the first plurality and the second plurality of fluorogenic compounds sensitive to a low intensity UV source.

14. The method as in claim 12 wherein determining the first plurality and the second plurality of fluorogenic compounds further comprises determining the first plurality and the second plurality of fluorogenic compounds sensitive to a high intensity UV source.

15. A fluorescent color calibrator for calibrating RGB pixel values, the fluorescent color calibrator comprising:
a substrate;
a plurality of fluorogenic compounds attached to the substrate and adapted to fluoresce in a visible color spectrum, wherein the plurality of first fluorogenic compounds comprises:
at least one substantially magenta fluorogenic compound;
at least one substantially orange-red fluorogenic compound;
at least one substantially yellow-orange fluorogenic compound;
at least one substantially yellow-green fluorogenic compound;
at least one substantially green fluorogenic compound;
at least one substantially blue fluorogenic compound;
a plurality of second fluorogenic compounds attached to the substrate and adapted to fluoresce in a visible gray spectrum, wherein the plurality of second fluorogenic compounds comprises:
a first substantially gray fluorogenic compound;
a second substantially gray fluorogenic compound exhibiting a darker gray fluorescence relative to the first substantially gray fluorogenic compound; and
an overlay cutout affixed to the substrate and adapted to allowing viewing of the plurality of first fluorogenic compounds and the plurality of second fluorogenic compounds.

16. The fluorescent color calibrator as in claim 15 further comprising a predetermined UV blocking agent layer adhering to the plurality of first fluorogenic compounds, wherein the UV blocking agent layer thickness is predetermined.

17. The fluorescent color calibrator as in claim 15 wherein the overlay cut-out further comprises a first fluorophor sensitive to UVA light sources.

18. The fluorescent color calibrator as in claim 15 wherein the overlay cut-but further comprises a second fluorophor sensitive to UVC light sources.

* * * * *